United States Patent [19]

Mamatov et al.

[11] 4,281,114
[45] Jul. 28, 1981

[54] METHOD FOR PREPARING DIFURFURYLIDENEACETONE OLIGOMER

[76] Inventors: Juldash Mamatov, ulitsa Pushkina, 50, kv. 60; Makhammadzhon Akhmadaliev, ulitsa Kuvasaiskaya, 203, kv. 27; Vladimir S. Kozhevnikov, ulitsa Pushkina, 64b, kv. 20, all of Fergana, U.S.S.R.

[21] Appl. No.: 136,699

[22] Filed: Apr. 2, 1980

[30] Foreign Application Priority Data

Apr. 10, 1979 [SU] U.S.S.R. .............................. 2741301

[51] Int. Cl.$^3$ .......................................... C07D 409/14
[52] U.S. Cl. ................................. 542/432; 260/347.8; 525/521; 525/940; 542/438
[58] Field of Search ................ 542/432, 438; 525/521, 525/940; 260/347.8

[56] References Cited

U.S. PATENT DOCUMENTS

| | | | |
|---|---|---|---|
| 2,853,469 | 9/1958 | Rosamilia | 525/521 |
| 2,853,470 | 9/1958 | Rosamilia | 525/521 |

FOREIGN PATENT DOCUMENTS 592747  9/1943  United Kingdom ..................... 542/438

OTHER PUBLICATIONS

Korshak et al., Chem. Abstracts 90(1979) #169474.
Korolkov et al., Chem. Abstracts 70(1969) #88368.
Kamenskii et al., Chem. Abstracts 55(1960) col. 11907.
Kulakov et al., Chem. Abstracts 75(1971) #77355.

*Primary Examiner*—Arthur P. Demers
*Attorney, Agent, or Firm*—Fleit & Jacobson

[57] ABSTRACT

A method for preparing difurfurylideneacetone oligomer which comprises heating difurfurylideneacetone with a moisture content of 15 to 40% at a temperature ranging from 80° to 90° C. under progressively increasing vacuum from the atmospheric pressure to 180–200 mm Hg, followed by the addition of a catalyst; as the latter use is made of hydroxides of alkali and/or alkali-earth metals at a weight ratio of difurfurylideneacetone to the catalyst of 1:0.005–0.04; then oligomerization of difurfurylideneacetone is carried out at a temperature ranging from 180° to 220° C.

1 Claim, No Drawings

METHOD FOR PREPARING DIFURFURYLIDENEACETONE OLIGOMER

The present invention relates to methods for preparing difurfurylideneacetone oligomers.

FIELD OF THE INVENTION

These oligomers are employed for the manufacture of a binder for graphitized plastics to be used in the production of chemically resistant antifriction and heat-conducting bushings, thrust bearings and chemically resistant lining plates.

Difurfurylideneacetone oligomer is obtained by way of a thermal or thermo-catalytic oligomerization of difurfurylideneacetone. The oligomer comprises a solid product melting upon heating and dissolving in organic solvents (acetone, chloroform and the like).

BACKGROUND OF THE INVENTION

Known in the art is a method for preparing difurfurylideneacetone oligomer under laboratory conditions. It comprises heating of difurfurylideneacetone in the presence of acid catalysts such as benzenesulphonic acid, metal chlorides at a temperature within the range of from 70° to 120° C. or without any catalyst at a temperature above 180° C. (cf. Plasticheskije massy, No. 12, 1960, p. 9–13, and No. 2 of the same Journal, 1974, p. 77). The process of oligomerization in the presence of said catalysts proceeds at a high rate thus hindering the process control and preparation of the desired products with the predetermined characteristics. Without catalysts the oligomerization process occurs at high temperatures and features a long duration (above 10 hours).

Known in the art is a method for preparing difurfurylideneacetone oligomer implemented on a pilot-plant scale. The method comprises charging difurfurylideneacetone in the form of a powder-like product containing no moisture into a reactor, melting at a temperature of 60°–65° C., heating at a temperature ranging from 120° to 130° C., followed by distilling-off low-molecular compounds, whereafter heating of the reaction mass is continued to a temperature within the range of from 200° to 210° C. with residence of the reaction mass at this temperature for a period of from 60 to 90 minutes until the oligomer is formed. The final oligomer is drained into pans and cooled to the ambient temperature.

This prior art method has certain disadvantages hampering its realization on a commercial scale, namely:

1. The process duration on the whole is 8–10 hours.
2. Carrying out oligomerization at a high temperature makes the process difficult to control due to the risk of a sharp elevation of temperature because of the exothermal character of the oligomerization reaction and outburst of the reaction mass out of the reactor. All this hinders the determination of the moment of the process completion and results in that different lots of the oligomer considerably differ from each other in their properties, i.e. the final desired product is unstable in respect of its characteristics.
3. Distilling-off low-molecular compounds from the dry difurfurylideneactone at a temperature of from 120° to 130° C. results in a sharp foaming of the reaction mass which is often accompanied by its outburst from the reactor.
4. Charging of the dry powder-like difurfurylideneacetone into the reactor is frequently accompanied by the formation of its aerosol which substantially impairs sanitary and hygienic conditions of labour.
5. Preparation of the dry monomer necessitates the stage of drying with the use of special drying unit. This complicates the process for the production of the oligomer and adds to its production costs.

Also known in the art is a method for the production of difurfurylideneacetone oligomer which consists in that the starting difurfurylideneacetone with a moisture content of from 150 to 40% is charged into a reactor and heated to a temperature of from 60° to 70° C. for melting. The molten furfurylideneacetone is heated at a temperature of from 80° to 90° C. under progressively increasing vacuum to 180–200 mm Hg. Then a catalyst is added, i.e. orthophosphoric acid in an amount of from 0.8 to 1.2% as calculated for the dry difurfurylideneacetone. The resulting reaction mass is heated to a temperature of 160°–165° C., followed by residence thereof at this temperature for a period of from 40 to 70 minutes, whereupon oligomerization of difurfurylideneacetone occurs.

This method for the production of difurfurylideneacetone oligomer is commercially realized; however, at the final stage the process of oligomerization of difurfurylideneacetone in the presence of an acid catalyst occurs but with a very high speed which hinders the possibility of determination of the degree of readiness of the oligomer. If the process is abruptly stopped (the reaction mass is sharply cooled) somewhat earlier, then an oligomer is obtained which has a low dropping point (75°–90° C.) hindering its processing.

If the process of oligomerization with an acid catalyst is not stopped at the stage of the oligomer readiness, then there occurs an uncontrollable reaction of polymerization of difurfurylideneacetone accompanied by a sharp elevation of temperature up to 200°–300° C. The resulting non-fusible and insoluble polymer is not suitable for any further processing.

The oligomer with the required properties has a life time of several minutes only (5–15 minutes), during which period it is impossible to determine its dropping point due to a long time required for the analysis. For this reason, the degree of readiness of the oligomer is defined by the increase in its brittleness in the cooled state by touch when continuously taking-off samples. In practical realization of this method, the quality of the obtained oligomer completely depends on the skill and experience of a person carrying out the synthesis of the oligomer of difurfurylideneacetone. By this method it is possible to obtain the oligomer with the maximum dropping point of 130°–140° C. This oligomer, when mixed with graphite in the manufacture of graphitized plastics, should be subjected to rolling for a period of 5 to 8 minutes. The modern processes for the manufacture of graphitized plastics contemplate a single passing of the material through rolls, i.e. rolling should be effected within several seconds. These requirements are met by oligomers with a dropping point within the range of from 150° to 170° C.

SUMMARY OF THE INVENTION

It is an object of the present invention to provide such a process for the preparation of difurfurylideneacetone oligomer which would make it possible to obtain the desired product having a substantially high dropping point and an increased molecular weight.

This and other objects of the present invention are accomplished by that in the method for preparing difurfurylideneacetone oligomer by heating difurfurylideneacetone with a moisture content of from 15 to 40% at a temperature within the range of from 80° to 90° C. under progressively increasing vacuum down to 180-200 mm Hg, followed by the addition of a catalyst to difurfurylideneacetone and oligomerization of the latter at an elevated temperature, in accordance with the present invention as the catalyst use is made of hydroxides of alkali and/or alkali-earth metals at a weight ratio between difurfurylideneacetone and the catalyst equal to 1:0.005-0.04 and oligomerization of difurfurylideneacetone is carried out at a temperature within the range of from 180° to 220° C.

The above-specified selected process conditions ensure the preparation of difurfurylideneacetone oligomer with the required range of its properties. Thus, lowering the catalyst amount below the above-specified lower limit results in slowing-down the oligomerization process and increase in its duration to 8 hours (instead of 40-120 minutes), while increasing the catalyst amount over the above-specified upper limit results in lowered physico-mechanical characteristics of the desired product. When the oligomerization temperature is increased, the resulting oligomer has a higher viscosity and a greater molecular weight which hinders processibility of the product.

The method according to the present invention makes it possible to produce difurfurylideneacetone oligomer with a new range of properties, namely: with a higher dropping point of 140°-180° C. (instead of 90°-140° C.) and a higher molecular weight of from 1,000 to 1,800 (instead of 600-800). The resulting oligomer has also a higher curing rate: it takes only several seconds instead of 5-8 minutes to cure the oligomer thus enabling a continuous process for making articles from the oligomer. Furthermore, difurfurylideneacetone oligomer produced by the method according to the present invention is twice more stable while under storage.

All this makes it possible to substantially enlarge the field of application of the oligomer and, in particular, it can be successfully employed in the production of materials useful in the manufacture of carbon-graphite equipment.

DETAILED DESCRIPTION OF THE INVENTION

The method for producing difurfurylideneacetone oligomer according to the present invention is simple and can be readily performed in the following manner.

Difurfurylideneacetone with a moisture content of from 15 to 40% is heated to a temperature of from 60° to 70° C. for melting, whereafter temperature is increased to 80°-90° C. with gradually increasing vacuum from atmospheric pressure down to 180-200 mm Hg to distill-off volatile components and water. Then vacuum is released, the catalyst is added and temperature is elevated to 180°-220° C. at the rate of 0.8°-1.2° C./min. At this temperature the oligomerization process is conducted for a period of from 40 to 120 minutes. During the oligomerization process, samples of the oligomer are regularly taken to determine its dropping point. Upon achievement of the required value of the dropping point the oligomer is discharged. The resulting product in the cooled form comprises a solid monolithic mass.

As the catalyst in the method according to the present invention use is made of hydroxides of alkali and/or alkali-earth metals such as sodium, barium, potassium, calcium at a weight ratio between difurfurylideneacetone and the catalyst equal to 1:0.005-0.04 (or the catalyst amount is 0.5-4.0% as calculated for dry difurfurylideneacetone).

For a better understanding of the present invention, some specific Examples are given hereinbelow by way of illustration.

EXAMPLE 1

Into a three-neck flask provided with a stirrer, thermometer, cooler, vacuum system and heating system, there are charged 800 g of difurfurylideneacetone with the moisture content of 15%. On completion of charging, the heater is switched-on and the flask contents are heated for melting at a temperature of 60°-65° C. for 10 minutes. After a complete melting of the mass, the stirrer is switched-on along with the vacuum pump and heat-treatment is conducted to distill-off volatile components and water at a temperature of from 80° to 90° C. with continuously increasing vacuum from the atmospheric pressure to 180-200 mm Hg. Then vacuum is released and, still under heating and stirring, sodium hydroxide is added in the amount of 0.6% by weight of dry difurfurylideneacetone (the weight ratio between difurfurylideneacetone and the catalyst is equal to 1:0.006). After charging of the catalyst temperature is elevated to 200° C. at the rate of 0.8°-1.2° C./min. The thermo-catalytic oligomerization is conducted at this temperature for 60 minutes. On expiration of this time period, the final product is discharged in the hot state and cooled to the ambient temperature. The properties of the thus-prepared oligomer are shown in Table 1 hereinbelow.

EXAMPLE 2

The process is conducted in a manner similar to that described in the foregoing Example 1. In doing so, use is made of difurfurylideneacetone with the moisture content of 25% and as the catalyst sodium hydroxide is employed in the amount of 0.5% by weight of the dry difurfurylideneacetone (the weight ratio between difurfurylideneacetone and the catalyst is equal to 1:0.005). The thermo-catalytic oligomerization is conducted at the temperature of 220° C. for 40 minutes.

Properties of the resulting oligomer are shown in the following Table 1.

EXAMPLE 3

The process is conducted in a manner similar to that described in Example 1 hereinbefore. Use is made of difurfurylideneacetone with the moisture content of 33.6% and as the catalyst sodium hydroxide is employed in the amount of 1% by weight of the dry difurfurylideneacetone (the weight ratio between difurfurylideneacetone and the catalyst is equal to 1:0.01). The thermo-catalytic oligomerization is conducted at the temperature of 180° C. for the period of 60 minutes.

The properties of the resulting oligomer are shown in Table 1 hereinbelow.

EXAMPLE 4

The process is conducted in a manner similar to that described in Example 1. Use is made of difurfurylideneacetone with the moisture content of 36.9% and as the catalyst potassium hydroxide is employed in the amount of 1% by weight of the dry difurfurylideneacetone (the weight ratio between difurfurylideneacetone and the catalyst is equal to 1:0.01). The thermo-catalytic oligomerization is conducted at the temperature of 220° C. for 60 minutes.

The properties of the resulting oligomer are shown in the following Table 1.

EXAMPLE 5

The process is conducted in a manner similar to that described in Example 1 hereinbefore. Difurfurylideneacetone used in this Example has the moisture content of 40% and as the catalyst a mixture of potassium hydroxide is employed in the amount of 0.5% by weight of the dry difurfurylideneacetone (the weight ratio between difurfurylideneacetone and potassium hydroxide is equal to 1:0.005) and barium hydroxide in the amount of 1% by weight of the dry difurfurylideneacetone (the weight ratio between difurfurylideneacetone and barium hydroxide is 1:0.01). The thermo-catalytic oligomerization is conducted at the temperature of 220° C. for 90 minutes.

Properties of the thus-prepared oligomer are shown in Table 1 hereinbelow.

EXAMPLE 6

The process is performed as described in Example 1. The starting difurfurylideneacetone has the moisture content of 17.5% and as the catalyst calcium hydroxide is employed in the amount of 4% by weight of the dry difurfurylideneacetone (the weight ratio between difurfurylideneacetone and the catalyst is 1:0.04). The thermo-catalytic oligomerization is conducted at the temperature of 220° C. for the period of 120 minutes.

The properties of the thus-prepared oligomer are shown in Table 1 hereinbelow.

EXAMPLE 7

The process is conducted as described in Example 1. The starting difurfurylideneacetone has the moisture content of 22% and as the catalyst a mixture of barium hydroxide is employed in the amount of 3% by weight of the dry difurfurylideneacetone (the weight ratio between difurfurylideneacetone and barium hydroxide is equal to 1:0.03) and calcium hydroxide in the amount of 1% by weight of the dry difurfurylideneacetone (the weight ratio between difurfurylideneacetone and calcium hydroxide is equal to 1:0.01). The thermo-catalytic oligomerization is conducted at the temperature of 220° C. for 90 minutes.

The properties of the thus-prepared oligomer are shown in Table 1 hereinbelow.

EXAMPLE 8

The process is conducted as described in Example 1. The starting difurfurylideneacetone has the moisture content of 28% and as the catalyst a mixture of sodium hydroxide is employed in the amount of 0.5% by weight of the dry difurfurylideneacetone (the weight ratio between difurfurylideneacetone and the sodium hydroxide is equal to 1:0.005) and calcium hydroxide in the amount of 0.8% by weight of the dry difurfurylideneacetone (the weight ratio between difurfurylideneacetone and the calcium hydroxide is equal to 1:0.008). The thermo-catalytic oligomerization is conducted at the temperature of 210° C. for 56 minutes.

The properties of the thus-prepared oligomer are shown in the following Table 1.

TABLE 1

Properties of difurfurylideneacetone oligomer prepared as in Example 1 through 8

| | Characteristics | | |
|---|---|---|---|
| Example No. | Dropping point, °C. | Gelation time at 200° C. in the presence of 4% of ferric chloride, seconds | Molecular weight |
| 1 | 176 | 46 | 1,684 |
| 2 | 180 | 32 | 1,800 |
| 3 | 146 | 143 | 1,096 |
| 4 | 164 | 99 | 1,579 |
| 5 | 155 | 104 | 1,497 |
| 6 | 153 | 112 | 1,500 |
| 7 | 140 | 128 | 1,000 |
| 8 | 171 | 53 | 1,766 |

The thus-prepared oligomers are used as a binder in the manufacture of graphitized plastics having the following properties:

| | |
|---|---|
| resilience | 2.6–3.6 kgf/cm$^2$ |
| Martens softening point, °C. | 240–296 |
| compression strength, kgf/cm$^2$ | 1,100–1,200. |

What is claimed is:

1. A method for preparing difurfurylideneacetone oligomer comprising heating difurfurylideneacetone with a moisture content of from 15 to 40% at a temperature ranging from 80° to 90° C. under progressively increasing vacuum from the atmospheric pressure to 180–200 mm Hg, adding a catalyst selected from the group consisting of hydroxides of alkali and/or alkali-earth metals at a weight ratio of difurfurylideneacetone to the catalyst of 1:0.005–0.04, followed by oligomerization of difurfurylideneacetone at a temperature ranging from 180° to 220° C.

* * * * *

UNITED STATES PATENT AND TRADEMARK OFFICE
CERTIFICATE OF CORRECTION

PATENT NO. : 4,281,114
DATED : July 28, 1981
INVENTOR(S) : JULDASH MAMATOV et al It is certified that error appears in the above—identified patent and that said Letters Patent is hereby corrected as shown below:

On the title page,

Section [30], change "April 10, 1979" to --April 6, 1979--.

Signed and Sealed this

Tenth Day of November 1981

[SEAL]

*Attest:*

*Attesting Officer*

GERALD J. MOSSINGHOFF

*Commissioner of Patents and Trademarks*